United States Patent [19]

Kokjohn et al.

[11] Patent Number: 6,090,588
[45] Date of Patent: *Jul. 18, 2000

[54] ISOLATED MELANIN-LIKE SUBSTANCE AND METHOD FOR PRODUCING THE SAME

[75] Inventors: Tyler A. Kokjohn, Glendale, Ariz.; John O. Schrader, Omaha, Nebr.

[73] Assignee: Board of Regents of University of Nebraska, Lincoln, Nebr.

[ * ] Notice: This patent issued on a continued prosecution application filed under 37 CFR 1.53(d), and is subject to the twenty year patent term provisions of 35 U.S.C. 154(a)(2).

[21] Appl. No.: 09/069,509

[22] Filed: Apr. 29, 1998

Related U.S. Application Data

[60] Provisional application No. 60/045,300, May 2, 1997.
[51] Int. Cl.[7] .............................. C12N 1/20; C12N 9/02; C12P 21/06
[52] U.S. Cl. .................. 435/71.2; 435/71.1; 435/108; 435/252.34; 435/253.6; 435/320.1; 435/975
[58] Field of Search .................................. 435/71.1, 71.2, 435/975, 252.34, 253.6, 320.1, 108

[56] References Cited

U.S. PATENT DOCUMENTS 5,474,933   12/1995   Weiner et al. .
5,846,531   12/1998   Weiner et al. .......................... 424/94.4

OTHER PUBLICATIONS

Kotob et al. Homogentisic Acid Is the Primary Precursor of Melanin Synthesis in *Vibrio cholerae,* a Hyphomonas Strain, and *Shewanella colwelliana.* Appl. Environ. Microbiol. Apr. 1995, vol. 61, Nos. 4, pp. 1620–1622, see entire document.

Coon et al. Homogentisic Acid is the Product of MelA, Which Mediates Melanogenesis in the Marine Bacterium *Shewanella colwelliana.* D. Appl. Environ Microbiol. Aug. 1994, vol. 60, No. 8, pp. 3006–3010, see entire document.

Studier et al. Use of T7 Polymerase to Direct Expression of Cloned Genes. Methods Enzymol. 1990, vol. 185, pp. 60–89, especially pp. 83–85.

*Primary Examiner*—Herbert J. Lilling
*Attorney, Agent, or Firm*—Shook, Hardy & Bacon L.L.P.

[57] ABSTRACT

The production of a melanin-like compound by introducing an inactivated virus into a culture of bacteria is disclosed. After introduction, the inactivated virus causes a phenotypic change in the bacteria. When introduced into a media containing tyrosine, these modified bacteria produce a melanin-like compound, pyomelanin. The bacteria will continue to produce pyomelanin until they are removed from the tyrosine source.

8 Claims, 1 Drawing Sheet

ISOLATED MELANIN-LIKE SUBSTANCE AND METHOD FOR PRODUCING THE SAME

This application claims the benefit of U.S. Provisional Application No. 60/045,300, filed May 2, 1997.

TECHNICAL FIELD

The present invention relates to the field of biotechnology and, more particularly, to a method for producing a melanin-like substance, pyomelanin, by treating certain bacteria with inactivated viruses and adding selected chemicals to the bacterial media, thereupon inducing the transformed bacteria to produce pyomelanin.

BACKGROUND OF THE INVENTION

Melanin is a naturally occurring compound commonly found in the skin, hair and retinas of humans and higher animals. Melanin is a protein comprised almost exclusively of the amino acid tyrosine and is synthesized by melanin-producing cells known as melanocytes in response to exposure to certain wavelengths of ultraviolet (UV) light. This reaction illustrates the primary utility of melanin; it is a tremendously effective absorber of UV light. UV light can be quite harmful to living organisms due to its propensity to cause cellular mutations, such as thymine dimers in DNA, which can cause melanoma and related skin cancers. Melanin is thus vital to the survival of many organisms.

Because melanin is such an excellent absorber of UV light, it has found a variety of industrial applications. In the cosmetics industry, for instance, melanin is used in makeup and other skin care products to provide greater UV protection to the user. Melanin is also used as a substitute for para-aminobenzoic acid (PABA), another compound that absorbs UV light. PABA can become toxic under certain conditions, which may lead to adverse reactions in some individuals. Melanin has also been used in paints, varnishes, and other surface protection formulations to provide greater UV protection to these surfaces. In addition, melanin has certain medical properties that allow it to bind a number of chemicals and drugs, thereby making it useful in the detection of low levels of compounds and metabolites, or in the elimination of toxic target Industrial production of melanin and melanin-like pigments have involved expressing a cloned gene in a bacterium or other microbe under complex and exacting conditions. Indeed, it is widely recognized that the isolation and purification of melanin require rather drastic procedures. Most melanin production involves the use of recombinant DNA technologies. These technologies usually require the activation of melanin production by the addition of an inducing agent. Cell cultures have also been used to produce melanin industrially, but again, these processes are complex and very expensive. Furthermore, melanin is not water soluble in its natural state. Technologies exist to make melanin water soluble, but these technologies involve the addition of chemicals such as trypsin or triethanolamine to solubilize the melanin.

Thus, until the advent of the present invention, industry and medical science have been confronted with a quandary: Melanin is a vital and useful substance, but expensive and complicated to obtain. The natural result of this dilemma is elevated costs. Melanin products and technologies relying on melanin have been offered to the public at high prices to offset the expense of obtaining melanin. Consumers, who benefit most from the use of melanin, have been forced to cover this expense. Given this price pressure, it is possible that some consumers have been unwilling or unable to pay the high price for melanin products and, as a result, have subjected themselves to harmful UV radiation which could have otherwise been avoided by use of such products. Over time, this could have serious health consequences.

SUMMARY OF THE INVENTION

It is therefore an object of the present invention to provide a method for producing a melanin-like compound that is simple, applicable to a wide range of tolerances and cost-effective.

It is another object of the present invention to provide a process for the production of massive amounts of a melanin-like compound from modified strains of bacteria.

It is also an object of the present invention to disclose a process to selectively regulate the production of pyomelanin by controlling the amount of activating substance contacting the modified bacteria.

It is yet another object of the present invention to disclose a modified strain of *Pseudomonas aeruginosa* that is resistant to UV radiation.

It is still another object of the present invention to disclose a unique, water soluble melanin-like compound exhibiting all or nearly all of the properties of melanin.

It is yet a further object of the present invention to provide a melanin substitute that can replace melanin in a wide range of applications in which melanin is currently used.

It is a related object of the present invention to provide a melanin substitute that can function as a UV absorbing agent in applications in which melanin is not or cannot be used.

To accomplish these and other related objects, the present invention relates to the production of a melanin-like compound by introducing inactivated bacteriophages or viruses into bacteria. The bacteriophages cause a phenotypic change in the bacterial cells. When introduced into a media containing tyrosine, these modified bacteria produce a melanin-like compound, or pyomelanin. The bacteria will continue to produce pyomelanin until they are removed from the tyrosine source. Using this simple and inexpensive process voluminous amounts of pyomelanin can be produced.

Additional objects, advantages and novel features of the invention will be set forth in the following description, and will become apparent to those skilled in the art upon examination of this disclosure.

DESCRIPTION OF THE INVENTION

Figure 1:
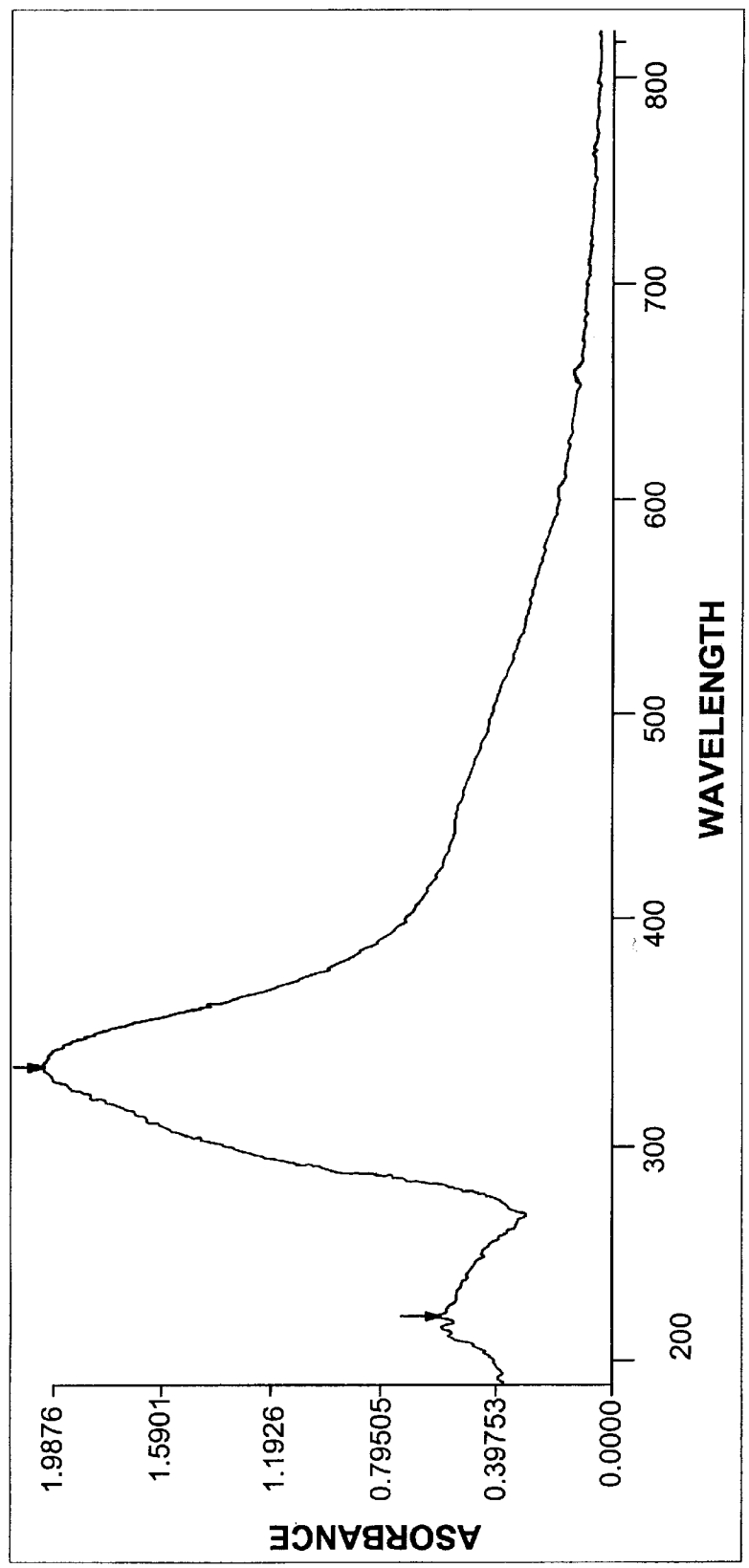
FIG. 1 is a graph showing the absorbance vs. wavelength of pyomelanin and illustrating the UV absorbing capabilities of pyomelanin.

The present invention relates to the production of a melanin-like compound, or pyomelanin, by the bacteria *Pseudomonas aeruginosa*. *Pseudomonas aeruginosa* is an excellent organism to use in the production of pyomelanin because it is plentiful, easy to work with and can grow under a variety of conditions. Other bacteria may also be somewhat effective for the production of pyomelanin, particularly other bacterial species within the genus Pseudomonas. Such bacteria are within the ambit of the present invention.

The bacteria are first treated with an inactivated form of either of the viruses known as UNL-1 or UT-1. UNL-1 and UT-1 are known viruses that are readily available to one of ordinary skill in the art from the Universities of Nebraska and Tennessee, respectively, and other sources. Samples of these viruses are stored at the University of Nebraska-Lincoln Department of Biological Sciences in several laboratory refrigerators and available for inspection. UNL-1 has been deposited with ATCC, 10801 University Blvd, Manassas, Va. 20110, USA and has been given Patent Deposit Designation PTA-469. In addition, other viruses have also been found to trigger a pigment-producing phenotypic reaction in bacteria. Such viruses are understood to be within the scope of this disclosure.

Because both UNL-1 and UT-1 are lethal to the bacterial cell, the viral cultures must first be inactivated. This inactivation may be accomplished by any of a number of well-known means. Preferably, inactivation of the viruses is achieved by exposing the viruses to UV-C light using any commercially available germicidal lamp. This process is best carried out by exposing virus lysates suspended at a concentration of $10^8$–$10^9$ viruses per milliliter in a solution of 0.85% (w/v) sodium chloride to UV-C radiation produced by a GE germicidal lamp for a period of time sufficient to apply a total UV-C dose 225–250 Joules/$m^2$. Exposure of the virus to this amount of UV-C radiation will serve to eliminate the ability of the virus to kill the host cell, but will not destroy all of the genetic material in the virus, nor will it interfere with the process of host cell infection or the ability of the infecting virus to inject DNA into the host cell.

After the viral culture has been inactivated, it is inoculated into a culture of bacteria, preferably *Pseudomonas aeruginosa*. *Pseudomonas aeruginosa* has specific receptors which will bind the inactivated viral particles and allow for the ultimate introduction of viral DNA into the host cell. This viral DNA may be incorporated into the overall genetic structure of the cell in a period of hours.

The bacteria surviving infection must then be isolated by mechanical methods to obtain the pyomelanin-producing strains. A lawn of the bacterial culture is formed on a Luria Broth (LB) agar plate, which includes 1% tryptone, 1% sodium chloride, 0.5% yeast extract and 1.2% Bacto agar. The lawn is formed by pouring a mixture comprising 0.1 ml of overnight culture of the bacteria in 2.5 ml melted lambda top agar on top of the already solidified LB agar plate. The lambda top agar comprises 1% tryptone, 0.5% sodium chloride and 0.65% Bacto agar. After the top agar has hardened, a 50 microliter sample of virus is placed on top of the lawn. The plate is incubated at 37° C. overnight. Bacterial survivors are observed the next day as clones growing in a clear zone produced on the bacterial lawn due to viral lysis. The survivors are streaked for isolation on a fresh LB agar plate and incubated for an extended period of 24–48 hours. Some of the survivors will produce pyomelanin and appear as brown colonies on LB agar plates.

It is necessary to streak the survivors for isolation and incubate for extended periods of time to observe the production of pyomelanin. This pigment production is not evident if the survivors are not removed from the original plate used for infection. This fact may explain why the production of pigment has not previously been noted after infection with certain bacteriophages, because it is necessary to specifically isolate and examine the survivors of infection to detect this phenotype.

These survivors, or modified bacteria, will produce pyomelanin when grown to the stationary phase in any suitable medium that contains at least 0.3% (w/v) tyrosine and is aerated. This may be accomplished by incubation of LB liquid cultures at a temperature of 37° C. for a period of 6–8 hours after inoculation. A small sample of overnight culture grown in dilute LB medium, 0.1 ml in 10 volume culture, provides a suitable inoculum. Any medium in which the bacteria are capable of growth is suitable. Once the culture reaches stationary phase, which is defined as the point at which cell numbers in the culture stop increasing, pigment production may be initiated by amending the medium with 0.3% tyrosine. Within 3 to 4 hours after introduction, the media will turn noticeably brown to the naked eye. No other inducing agent, other than those normally produced by the culture as it enters stationary phase, is necessary to initiate the pyomelanin producing mechanism in the modified bacteria.

The production of pyomelanin can and will continue until all of the tyrosine in the liquid culture is converted into pyomelanin by the modified bacteria. The process can be easily stopped by removing the tyrosine-containing media or by removing tyrosine from the media. The cells will begin producing pyomelanin again once they are reintroduced to any type of media containing tyrosine. The modified bacterial cells maintain the potential to produce the pigment indefinitely, so simple maintenance of stock cultures on appropriate media will ensure the ability to produce large, and potentially indefinite, amounts of pyomelanin.

An ideal process for pyomelanin production by the modified bacteria involves adding tyrosine-containing media to a bioreactor where it is incubated and mechanically mixed with the modified bacterial cells. The cells and medium may be placed in a Cy tolift™ bioreactor in which the modified bacteria are maintained in suspension and the medium aerated with entry of filtered sterile air. The system may be operated as a sequencing batch reactor in which cells are incubated until pigment production is maximal, and at that point aeration is halted. The cells are allowed to settle, and the supernatant containing the pigment is decanted. A new cycle may be initiated by allowing fresh medium to enter the reactor.

Another method of operation is to entrain the cells in a device that will permit entry of medium to the cells, but not allow the cells to leave the containment vessel. Cells may be placed in sterile containers covered with 0.45 micrometer nitrocellulose filters and submerged in larger containers of the medium in which pigment formation is desired.

The pyomelanin produced by this process also contains a certain quantity of pyocyanin. The pyomelanin can be purified by extracting it with equal volumes of chloroform to remove pyocyanin and any other pigments in the supernatant. Pyomelanin is not soluble in organic solvents, such as chloroform, and remains in the aqueous layer. The extracted pyomelanin may be concentrated by evaporation of the remaining water.

Pyomelanin has been found to be extremely similar to melanin, particularly in terms of UV absorption. The properties of this pyomelanin pigment allow it to provide excellent protection from the deleterious effects of UV-A and UV-B light radiation. The compound effectively absorbs solar UV wavelengths between 300 to 400 nanometers, with a peak absorption at 350 nanometers, as shown in FIG. 1. Pyomelanin is also water soluble.

Several samples of pyomelanin produced in accordance with the method of the present invention are stored at the University of Nebraska-Lincoln Department of Biological Sciences. Because pyomelanin can be quickly produced using the method disclosed herein and readily available components with no undue experimentation, no deposit of the substance has been made. A deposit can and will be made if deemed necessary.

In addition, the modified bacteria themselves show a tremendous phenotypic change in their ability to survive exposure to UV radiation. The following graph presents data on the survival characteristics of unmodified *Pseudomonas aeruginosa*, strain PAO1, and *Pseudomonas aeruginosa*, strain PA101, as modified with inactivated UNL-1.

| PAO1 | | PAO1 (Modified with UNL-1) | |
|---|---|---|---|
| Time of exposure | % Survival | Time of exposure | % Survival |
| 0 min | 100% | 0 min | 100% |
| 30 min | 7.7% | 30 min | 74% |
| 60 min | 1.4% | 60 min | 74% |

As shown by this graph, UV radiation is highly damaging to the unmodified bacteria, resulting in nearly 99 percent mortality after 60 minutes. Bacteria modified in accordance with the present invention, though, exhibit nearly 75 percent survival over the same time period. It is important that laboratories be equipped with techniques to enable bacterial cell s to avoid sunlight damage for use in environmental applications. In particular, such a technique would be highly valuable for use in *Pseudomonas aeruginosa* used in bioremediation. The pyomelanin produced by the modified bacteria will, in the environment, diffuse from the modified bacteria over a certain period and help to protect other bacteria in the vicinity. It is thought that much of the real bioremediation in nature is accomplished not by pure cultures of specialized bacteria, but rather by consortia of bacterial species. In this general role, pigment-producing *Pseudomonas aeruginosa* may, if used in concert with other microbes, act to protect entire communities of these bioremediative microbes from the deleterious effects of sunlight.

The present invention does not require the use of recombinant DNA technology, nor the use of any exogenous inducing treatments to the modified bacterial cultures described herein to initiate gene expression. These features help to lessen costs associated with the production and operation of any fermentation system incorporating the method of the present invention. In addition, the process is quite uncomplicated, allowing for easy incorporation into industry practice.

This pyomelanin compound shows the potential to be used in every application for which melanin and other melanin-like compounds are currently used. The method for producing pyomelanin of this invention, however, is superior over existing methods for melanin production for a number of reasons: First, the pyomelanin of the present invention is derived solely from a prokaryotic organism. Second, no recombinant DNA is involved in the creation of the producer strains of the bacteria. Third, the pyomelanin producing strains of the bacteria make pigment under easily controlled and inexpensive conditions. Fourth, the modified strains do not need to be managed for optimum rapid growth. Fifth, the media used for producing pyomelanin is inexpensive and supports avid pigment production. Sixth, no exogenous inducing agent addition is necessary for pyomelanin production using the process of this invention.

The pyomelanin production of the present invention is amenable to large scale operations, including those that occur outside controlled environments. The process requires only an aerobic culture of cells in stationary phase with a sufficient source of tyrosine to perpetuate pyomelanin production. Temperature is not critical to the process. In addition, tyrosine is plentiful in many waste products. Using the process of the present invention, it is possible to set up large scale pyomelanin production operations in sewage or waste oxidation ponds at bioprocessing facilities, such as rendering plants, hide processing units, gelatin manufacturers, packing plants. This would be the most efficient processing of waste possible.

There are numerous other applications for the pyomelanin production process of the present invention. For example, one could extend the active periods of waste oxidation lagoons in temperate zones because dark pigment absorbs sunlight, thereby keeping the water warm and maintaining the system active and aerobic. The sunlight absorbing utility of pyomelanin could be used to augment salt de-icing in winter or to augment solar heating devices. Pyomelanin could also be sprayed on plants to stop sun-induced shock when they are moved from the greenhouse to the field. Because pyomelanin is a catechol-based compound, there is a possibility that plants will absorb it directly and produce their own sunblock. This might be important in preventing sunburn or sun trauma in crop plants.

Perhaps most importantly, the ease and low cost of producing pyomelanin using the method of the present invention can dramatically reduce the cost of UV protection in numerous consumer products. By eliminating or reducing cost barriers to such products, it is hoped that more consumers will avail themselves of UV protection in the form of UV reducing cosmetics and sun screens. It is the ultimate goal of the present invention that, by improving accessibility to these products, it may help to reduce the likelihood of skin cancer and other serious illness.

Having described the invention, the following is claimed:

1. A method for producing pyomelanin comprising:
   providing a bacteria;
   providing an inactivated virus;
   inoculating the bacteria with the inactivated virus;
   allowing the inactivated virus to be incorporated into the bacteria to create a modified bacteria;
   contacting the modified bacteria with an amino acid source to initiate pyomelanin production; and
   recovering pyomelanin from the modified bacteria.

2. The method of claim 1 wherein the bacteria is *Pseudomonas aeruginosa*.

3. The method of claim 2 wherein the inactivated virus is UNL-1.

4. The method of claim 3 wherein the amino acid source contains tyrosine.

5. The method of claim 4 further comprising the step of terminating the production of pyomelanin by removing the modified bacteria from the amino acid source.

6. A method for producing pyomelanin comprising:
   providing a culture of *Pseudomonas aeruginosa*;
   providing inactivated UNL-1 virus;
   introducing the inactivated virus to the culture of *Pseudomonas aeruginosa*;
   allowing the inactivated virus to be incorporated into the *Pseudomonas aeruginosa* to create a modified bacteria;
   contacting the modified bacteria with a media containing tyrosine to initiate pyomelanin production; and
   recovering pyomelanin from the modified bacteria.

7. The method of claim 6 wherein the inactivated virus is treated with ultraviolet light for a sufficient time to inactivate the plaque-forming ability of the virus.

8. The method of claim 7 further comprising terminating the production of pyomelanin by removing the modified bacteria from the media.

* * * * *